United States Patent [19]

Caskey et al.

[11] 4,447,598

[45] May 8, 1984

[54] METHOD OF PREPARING EPOXY RESINS HAVING LOW HYDROLYZABLE CHLORIDE CONTENTS

[75] Inventors: Terrence L. Caskey, Concord; Theodore L. Parker, Lafayette; Patrick H. Martin, Danville, all of Calif.

[73] Assignee: The Dow Chemical Company, Midland, Mich.

[21] Appl. No.: 482,760

[22] Filed: Apr. 7, 1983

[51] Int. Cl.$^3$ .............................................. C08G 59/14
[52] U.S. Cl. .................................... 528/489; 525/507; 525/523; 528/87; 528/98; 528/99; 528/405; 549/517
[58] Field of Search .................. 525/507, 523; 528/87, 528/98, 405, 99, 489; 549/517

[56] References Cited

U.S. PATENT DOCUMENTS 4,132,718 1/1979 Vargiu et al. ...................... 528/95 X
4,394,496 7/1983 Schrader .............................. 528/112

*Primary Examiner*—Earl A. Nielsen

[57] ABSTRACT

The hydrolyzable "chloride" contents of epoxides prepared from epihalohydrins and phenols, aromatic amines or >N-H group-containing heterocycles are considerably reduced by a second dehydrochlorination step which comprises dissolving the epoxide in a solvent having the characteristics of a 1:1 by weight blend of methylethylketone and toluene and treating it with amounts of base and water ensuring a final base concentration equivalent to that of about 4 wt. % aqueous NaOH.

11 Claims, No Drawings

METHOD OF PREPARING EPOXY RESINS HAVING LOW HYDROLYZABLE CHLORIDE CONTENTS

BACKGROUND OF THE INVENTION

"Epoxidation" of mono- and polyfunctional phenols or aromatic amines, hydantoins and triisocyanuric acid by reaction thereof with epihalohydrins (epichlorohydrin most notably) is well known. Ordinarily, the epoxidation proceeds through two successive reactions; adduction and dehydrohalogenation:

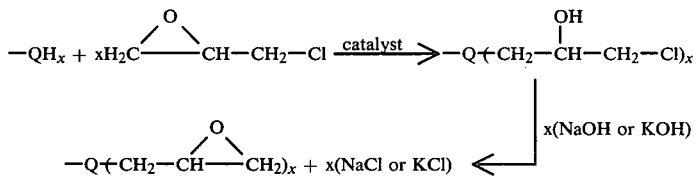

wherein —$QH_x$ is —OH, —$NH_2$,

or >NH, R is a non-interfering radical and the first reaction is catalyzed by an onium salt or an alkali metal hydroxide (conveniently, the same as that employed in the second reaction).

Henceforth in these specification what is said about the epoxidation of phenolic —OH groups will be intended to apply as well to —$NH_2$ and >NH groups, unless otherwise noted. Thus, the term "epoxidation product" is intended herein to mean a compound comprising a plurality of oxirane groups, at least one of which is contained in a glycidyl group derived from the dehydrohalogenation of an adduct of the oxirane ring in an epihalohydrin with an active hydrogen-containing group, such as, for example, an —OH, —$NH_2$ or —NH- glycidyl group attached to an aromatic ring or an >N-H group in which the >N— is part of an N-heterocyclic ring.

The term MEK is used herein to represent methylethylketone.

Little difficulty is ordinarily encountered in completing the foregoing second step in the epoxidation of otherwise unsubstituted monofunctional hydroxy benzenes (etc.). However, completion of dehydrohalogenation is more difficult when the phenol or amine already contains one or more glycidyl, glycidylamino or glycidyloxy groups. This is most noticeably the case when the epoxidation is carried out in a manner such that a preponderantly oligomeric product is formed (by in situ reaction of polyfunctional epoxides with unepoxidized starting phenols (etc.)). By resort to higher temperatures and caustic concentrations it is possible to push the dehydrohalogenation more nearly to completion. This technique reduces the content of "hydrolyzable chloride" in the product, but is of limited utility because it is also conducive to base-catalyzed oxirane-consuming reactions. The latter reaction results in polymerization and, when species having an oxirane functionality greater than two are present, in crosslinking; gelation of the reaction mass then may occur.

The difficulty of attaining low hydrolyzable chloride levels is greater when the structure of the starting phenol (or at least of any oligomeric halohydrin intermediate species) is inherently such as to hinder or retard dehydrohalogenation. Exemplary of such starting phenols are phenol/formaldehyde novolacs and poly(hydroxyphenyl)alkanes having functionalities of three or more.

The predominant source of hydrolyzable chloride (C-Cl groups) in glycidyl ether type epoxides is the presence of intermediate 1,2-halohydrin intermediate molecules which can be but have not been dehydrohalogenated. However, by-product species which do not have a hydroxyl group α to the C-Cl group and cannot be converted to 1,2-epoxides also constitute a source of hydrolyzable chloride. The process of the invention conveniently is referred to as a re-dehydrohalogenation step but is not limited to reactions with C-Cl species convertible to epoxides by reaction with a base.

Certain oligomeric epoxides of the latter type are prepared from 1,1,1-tri(hydroxyphenyl)alkanes. These epoxides are resins having a unique combination of properties which make them particularly suitable in curable formulations for encapsulation of electronic components which will be exposed to severe temperature and moisture conditions. (These epoxides are dislosed in U.S. Pat. No. 4,394,496, Ser. No. 316,586, filed Oct. 30, 1981.) For the latter use, the epoxide must have a low melt viscosity and a very low hydrolyzable chloride content. Because the viscosity must be held down, resort cannot be had to the conventional techniques-which may be employed to lower chloride levels at the expense of a substantial molecular weight increase-even though gelation is avoided. Thus, it would be highly desirable to find a way of modifying known epoxidation procedures to permit attainment of low chloride contents without experiencing substantially higher viscosities. To do this would be particularly valuable in the case of epoxies prepared from tri(hydroxyphenyl)methanes.

The epoxidation process claimed in the '496 patent identified earlier herein is directed to the preparation of epoxides from tri(hydroxyphenyl)methanes (in which the remaining methane hydrogen may be replaced by alkyl radicals of up to 10 carbons). However, the process is believed to be generally advantageous for the epoxidation of phenols, aromatic amines and >NH groups in heterocyclic rings.

Thus, the latter process may be generally defined as the method of preparing a polyepoxide which comprises: (1) reacting a polyfunctional phenol, aromatic amine or a nitrogen heterocycle in which a reactive hydrogen is attached to each of two or more ring nitrogens, with an epihalohydrin in the presence of more than 1 and up to about 3 equivalents per —OH or >N-H group of an aqueous base and essentially in the absence of coupling catalysts and solvents other than the epihalohydrin itself; (2) adding a solvent having the characteristics of a methylethylketone/toluene mixture and up to about 2 more equivalents of aqueous base; and (3) dehydrohalogenating the products of step (1) with the base present after step (2).

The following example of the foregoing process, as applied specifically to the epoxidation of 2,4',4''-trihydroxytriphenylmethane, is given in the '496 patent and constitutes the nearest prior art known of to the present applicants.

"Epichlorohydrin (114.1 grams, 1.23 moles) was added to 100 grams (0.342 moles) of 2,4',4''-trihydroxytriphenyl methane (an equivalent ratio of (1.23/(0.342×3)=1.2:1). The resulting mixture was heated moderately and stirred until the starting material dissolved in the epichlorohydrin. After elevating the temperature to about 90° C., the rate of stirring was increased and 51.5 grams (1.29 moles) of NaOH (1.29/(0.342×3)=1.25 moles per phenolic hydroxyl in the starting material) was added portionwise, as a 25% aqueous solution, over a one-hour period. When addition of about 60% of the NaOH solution was completed, 100 ml (80 grams) of a 3:1 mixture of methylethylketone and toluene was added to the reaction mixture and the NaOH addition continued. Following the solvent mixture addition, the temperature of the reaction mixture decreased from about 100° to about 85° C. After the NaOH addition was completed, the reaction mixture was heated with stirring at 80°-85° C. for another 90 minutes and then mixed with another 200 ml (160 grams) portion of the solvent mixture and 50 ml of water. A concentrated brine, which formed at the bottom of the mixture, was separated therefrom. Solvent was then stripped (*) from the reaction mixture (under 20-25 inches of vacuum), with final removal of volatiles being done by steam stripping under vacuum. As a result of these operations, a clear, amber, hard and brittle resin with an Epoxy Equivalent Weight (EEW) of about 215-240, a melt viscosity of 500-1000 centistokes at 150° C., and a Duran softening point of 80°-85° C. was obtained. Based on the EEW, the average epoxy functionality appears to be that of a dimer (theoretical EEW=216), e.g., epoxide functionality of about 4. However, from the results of GPC (Gel Permeation Chromatographic) analysis, it appears the monomer and dimer each comprise about 20-25% of the product while the trimers and tetramers together comprise about 50-60%. Various 2 gram samples of the resin were mixed with stoichiometric amounts of a curing agent (methylene dianiline) and cured for 2 hours at 90° C., 4 hours at 165° C. and 16 hours at 200° C. Heat distortion temperatures were determined by the known TMA method and found to range from about 245°-253° C. Similar TMA tests on the cured tris-epoxide of leucaurin of Example 3 were found to be about 246° C.
*Note: If the wet organic phase has not already been dried, the water content obviously will be removed in the early stages of stripping and the salt it held will precipitate. If a salt-free product is desired, stripping of course can be interrupted and the precipitate filtered out.

When the foregoing preparation is carried out in essentially the same manner otherwise but at an epi to phenolic hydroxyl ratio of 1.5, the EEW of the product drops to about 205, the monomeric epoxide content rises to about 30%, and the viscosity of the product decreases accordingly to about 400 c.s."

OBJECTS OF THE INVENTION

1. The primary object of the present invention is to provide a better technique for reducing hydrolyzable chloride contents in epoxy resins.
2. Another object is to effect an improvement, in the latter regard, in the preparation of polyfunctional epoxides from aromatic or heterocyclic phenols, amines or >NH compounds.
3. It also is an object to reduce said chloride contents without paying a penalty in the form of substantially higher contents of higher oligomers and/or cross-links.
4. A further object is to provide a method of upgrading an already made epoxy resin by reducing the hydrolyzable chloride content therein.
5. Since hydrolyzable "chloride" is objectionable primarily as a source of chloride ion, a corollary object is to reduce the content of both hydrolyzable and ionic chloride in epoxy resins.

Still other objects will be made apparent to those knowledgeable in the art by the following specifications and claims.

SUMMARY OF THE INVENTION

It has now been demonstrated that the foregoing objects can be realized, with regard to the preparation of monomeric or oligomeric epoxides from tri(hydroxyphenyl)alkanes, by employing a modified version of the process defined earlier herein. It is believed that said objects can similarly be realized in the epoxidation of phenols, aromatic amines and N-heterocycles in general or in post-epoxidation treatment of polyepoxides prepared with epihalohydrins.

That is, the invention, in its broadest aspect, is a method of reducing the hydrolyzable chloride content of an epoxidation product, without substantially altering it otherwise, said method comprising
(1) providing a two-phase mixture of
  (a) an organic phase which is a solution of said product in a solvent having the characteristics of an MEK/toluene blend in which the MEK/toluene wt. ratio is within the range of from about 40/60 to about 55/45, and
  (b) an aqueous solution of from about 1 to about 3 equivalents of base per equivalent of hydrolyzable chloride in said product, the amount of water in the latter solution being such that the base concentration therein will not be less than equivalent to 4 wt. % aq. NaOH after completion of the following step, and
(2) intimately intercontacting said phases, at an elevated temperature, until the hydrolyzable chloride of said product has decreased to a satisfactory extent.

The treated product is preferably recovered by neutralization of the final reaction mixture—advantageously with $CO_2$; drying of the neutralized mixture—preferably by azeotropic distillation (stripping)—and filtering out the resultant precipitate of salt; and, steam-stripping to complete volatiles removal.

The most preferred application of the process of the invention is in-situ subjection of a nascent epoxidation product to a second dehydrochlorination.

DETAILED DESCRIPTION

Suitable epoxidation products for the practice of the present invention are those which have low or negligible contents of epihalohydrins and are soluble in solvents having the characteristics of MEK/toluene blends in which the MEK content is from about 40 to 55 wt. % and the balance is toluene. It is of course essential that the product not contain anything capable of causing detrimental reactions between any of the components of the starting solution to proceed to an intolerable extent during the chloride-reducing treatment. In the latter regard, it may be noted that methods of removing onium-type catalysts from epihalohydrin/phenol reaction mixtures are known.

Experience so far has been that the process of the invention, at least as applied to treatment of oligomeric epoxidation products of tri(hydroxyphenyl)methanes, does not reduce chloride levels below about 180 ppm at practical rates. Accordingly, epoxidation products having hydrolyzable contents in excess of 200 ppm are preferred for the practice of the invention.

Preferably, the epoxidation product is a polyfunctional epoxide prepared by the generalized version given earlier herein of the process disclosed in the '496 patent identified earlier herein. Such products advantageously are still dissolved in the solvent (preferably, MEK/toluene) in which they were formed and have been largely freed of epihalohydrins and salts. The present process is particularly valuable as a second dehydrochlorination step in the preparation of an oligomeric polyepoxide, i.e., one comprising a high proportion of molecules, each of which is derived from several molecules of the polyfunctional —OH and/or >NH compounds charged to the epoxidation reaction.

A preferred class of epoxidation products are $C_1-C_3$ alkanes substituted with three or four hydroxyphenyl groups. Among these, the 1,1,1-tri(hydroxyphenyl)alkanes, particularly the methanes, are most preferred.

Various representative types of compounds from which suitable epoxidation products may be derived by reactions with an epihalohydrin and a base are listed at the end of these specifications.

Suitable reaction media for the process of the invention are solvents or solvent mixtures having the characteristics of a blend of MEK and toluene which are essential to the process. The medium of choice is a blend of MEK/toluene—preferably in a weight ratio ranging from about 40/60 to about 55/45. The range from about 49/51 to 51/49 is more preferred and the ratio of about 50/50 is most preferred. As disclosed in the '496 patent identified earlier herein, MEK/toluene blends exhibit growth-limiting and sidereaction inhibiting characteristics when employed as reaction media for epoxidations of tri(hydroxyphenyl)methanes (blend ratios in the range of from about 2/1 to about 4/1 being preferred for the preparation of the oligomeric products). Other characteristics of such blends which are highly desirable for a second dehydrochlorination step in which substantial molecular weight growth is to be avoided are relatively low reflux temperatures (initial boiling points of about 80° C.) and formation of a ternary azeotrope with water. That is, it is easy to maintain a reaction temperature at which epoxide consuming reactions are not fast and to rapidly dry the final reaction mixture at a comparable temperature, by azeotropic distillation.

Another highly desirable characteristic of MEK/toluene blends is the ready filterability of the salt precipitates which form as the water content of the organic phase of the dehydrochlorination mixture is reduced (whether by azeotropic distillation or by other means, such as contacting with $MgSO_4$, for example).

As applied to chloride content reductions in epihalohydrin-derived epoxides in general—including those which are nominally difunctional (actually about 1.5-1.7, usually), other solvents exemplary of those which may have the foregoing characteristics to a useful degree are diethylketone/toluene, methylpropylketone/xylenes, cyclohexanone/toluene, "glyme" (the dimethyl ether of ethylene glycol)/toluene, a blend of tetrahydrofurfuryl alcohol methyl ether or tetrahydropyran with anisole); and methyl isobutyl ketone alone.

Suitable bases are those which are of sufficient water solubility and base strength to meet the specifications of clause (b) in step (1) of the foregoing summary definition of the invention. For the treatment of most epoxidation products, the most economic and otherwise suitable type of base will be an alkali metal hydroxide such as, for example, KOH or NaOH—the latter being preferred. However, alkaline earth metal hydroxides such as $Ca(OH)_2$ and $Ba(OH)_2$ are also considered generally suitable. In those applications where the presence of ammonium base residues in the final reaction product is not objectionable, a nitrogen base such as $NH_4OH$ or choline(2-hydroxyethyl, trimethyl ammonium hydroxide) may be employed.

Suitable base to hydrolyzable "chloride" equivalent ratios lie generally within the range of from about 1 to about 3, as indicated earlier herein. Although it is feasible to operate at substantially higher ratios, neutralization of the excess base will generally be essential and the process will become both wasteful and expensive. Thus, it is preferred to employ less than two equivalents of base. It is desirable to employ at least 1 (preferably about 1.4 or more) equivalents since maximal (and rapid) dehydrochlorination ordinarily will be sought. Accordingly, the ratio preferably is within the range of from about 1.4 to about 1.6. That is, the amount of base charged to the reaction will be such as to provide from 1.4 to about 1.6 equivalents of hydroxide per equivalent of basehydrolyzable

in the epoxidation product.

Base concentration

The initial concentration of base in the aqueous phase of the (re)-dehydrochlorination mixture is determined by the excess (up to 100%, ordinarily) of base charged over the stoichiometric amount for the reaction and by the amount of water which can be present without reducing the final base concentration below a level at which the hydroxyl ion content will be the same as for 4 wt. % aq. NaOH. The reaction rate becomes impractically low if the base concentration falls below the latter level. On the other hand, it is desirable to consume most of the charged base in the dehydrochlorination reaction, thereby minimizing the amount that must be neutralized. Accordingly, it is preferred to establish an initial concentration of base such that the final concentration will be the same as that in 4-4.5% aq. NaOH.

The relationship of initial base concentration to the % excess of base employed, for a final NaOH concentration of 4 wt. %, is illustrated below.

| % xs NaOH | Initial NaOH Concentration, % |
|---|---|
| 10 | 31.42 |
| 50 | 11.11 |
| 100 | 7.69. |

Neutralization

The unconverted base in the final reaction mixture can be neutralized with any otherwise suitable acid-source material. However, $CO_2$ is highly preferred. It is cheap, can be introduced simply by pressurization of the vapor space in the reactor, and cannot be taken up in any substantial excess, i.e., cannot result in acidification to any significant degree. The neutralization products (carbonates and/or bicarbonates) are useful and pose substantially less of a disposal problem than chlorides or sulfates. (To the best of the present Applicants' knowledge, it has not previously been proposed to use $CO_2$ for neutralization of epoxidation (dehydrochlorination) mixtures.)

To allow time for adequate mass transfer between the gas phase ($CO_2$ bubbles passing through the reaction mixture or $CO_2$ in the vapor space above it) and the dispersed, aqueous phase, a neutralization period of at least 20 minutes should ordinarily be allowed. To ensure complete neutralization, times of 30 minutes are better.

Suitable reaction temperatures range from about 50° C. up to about 150° C. or more—depending on the functionality and thermal stability of the epoxide (epoxidation product) being treated. That is, the more highly functional epoxides will generally be more prone to oligomerization. When temperatures in the vicinity of 125°–150° C. are employed, use of more than about a 50% excess of base may be undesirable. In order to control the reaction temperature by refluxing, resort to reduced pressures will be necessary when the desired temperature is below the boiling point of the lowest-boiling component of the reaction medium. Since it is more than ordinarily desirable to push the reaction to completion as rapidly as possible in order to minimize oligomerization, temperatures of at least 75° are preferred. On the other hand, temperatures above about 85° are generally less preferred—particularly in treating tri- or tetra(glycidyloxyphenyl) alkanes or epoxy novolacs.

Super-atmospheric pressures—at least equal to the autogenous pressure developed—are of course required at temperatures greater than about 100° C.

Suitable contact times range from those which suffice to effect some reduction in hydrolyzable chloride contents to those beyond which the reaction does not proceed at a useful rate. As a general rule, contact periods of from about 40 to about 80 minutes (depending inversely on the reaction temperture) will result in final hydrolyzable chloride contents of about 200 to 180 ppm. Periods of about 55 to about 65 minutes are preferred as providing for high chloride conversions without resulting in substantial oligomerization (or further oligomerization of an oligomeric epoxidation product).

"Straight-through" preparation of low chloride epoxidation product constitutes the most preferred embodiment of the present invention. In this embodiment, the normal two-step epoxidation procedure is followed by a second, in-situ, dehydrochlorination. The nearest prior art process is that disclosed in the '496 patent for the preparation of "tris resins" or tri(glycidyloxyphenyl)methanes, preferably as oligomeric products. The overall "straight-through" process here disclosed differs in several respects from the prior art process as ordinarily practiced for the manufacture of the tris resins: (1) a higher epihalohydrin to phenolic hydroxyl ratio is employed, i.e., about 1.45–1.55, rather than 1.20–1.25, in order to limit molecular weight growth and hold down product viscosity; (2) the proportion of toluene in the toluene/MEK reaction medium is higher, i.e., 1:1 vs 1:3, thereby permitting faster water removal from the epoxidation mixture (by azeotroping) and improving the solvent action of the solvent mixture; (3) extra MEK/toluene is added, as a third increment. This permits rapid, essentially complete, azeotropic water removal without having to return MEK/toluene condensate (which is not only wet but usually contains some of the epihalohydrin—an eventual source of hydrolyzable chloride) in order to have an organic phase from which the salt precipitated in drying can readily be filtered out; (4) the use of $CO_2$ for neutralization (after the second dehydrochlorination) avoids the risk of overshooting on acidification; and (5) resort to steam stripping in the final stage of devolatilization speeds up stripping without overheating the resin. The net result of all of the foregoing improvements (including the second dehydrohalogenation) is a practical way to prepare polyepoxides having both low melt viscosities and low chloride contents.

Agitation of the reaction mixture is essential to intimate inter-contacting of the two phases. This may be accomplished by boiling action (refluxing), stirring or pumping.

EXAMPLES

The following examples are for purposes of illustration and are not to be construed as limiting the scope of the invention in a manner inconsistent with the claims appended to these specifications.

EXAMPLE 1

Post-treatment of Pre-formed Epoxide

An oligomeric epoxidation product prepared from 2,4',4''-trihydroxy-triphenylmethane essentially in the manner of the prior art example reproduced in the Background discussion herein had a hydrolyzable chloride content of about 800 ppm. After post-treating this product with aqueous NaOH in 1:1 MEK/toluene, separating the organic and brine phases, azeotropically drying and filtering the organic phase and steam stripping the filtrate, the treated resin was found not to have substantially increased in melt viscosity and to have a hydrolyzable chloride content of less than 300 ppm.

EXAMPLE 2

Epoxidation of 2,4',4''-trihydroxy-triphenyl methane in 1:1 MEK/toluene and in-situ base treatment of the resulting oligomeric product.

A 1000 gal. reactor was charged with the "trisphenol", 1000 lbs., and epichlorohydrin, 1400 lbs., then agitated and heated at reflux (~119° C.) until all trisphenol was dissolved. The solution was then cooled to 100° C. in a closed system, thereby creating a negative pressure to hold down the pressure developed in response to the exothermic nature of the reaction resulting from the caustic addition and 25% wt. caustic was pumped into the solution, a total of 2712 lbs. in 60 min. The reaction was held at reflux. After 50% of the total caustic charge had been pumped in, a solvent addition of 50/50 MEK/toluene, 1000 lbs., was made without interrupting the caustic addition. After all the caustic had been added, the reaction was held at reflux for 90 minutes additional. More 50/50 MEK/toluene, 2000 lbs., and water, 1000 lbs., was added with gentle agitation. The phases were allowed to separate and the lower brine layer drained off. Another 1000 lbs. of 50/50 MEK/toluene was added, then the system was heated and water azeotroped off (head temperature ~80° C.) until 30 liters of water had been collected. The resin solution was titrated for hydrolyzable chloride and 25% aqueous NaOH added in an amount such that the initial concentration in the aqueous phase was about 10 wt. % and the final concentration would be 4% (if all of the hydrolyzable chloride were converted). The reactor contents were held at reflux (head temperature about 80°) for one hour, neutralized with $CO_2$ under pressure for one-half hour, then returned rapidly to boiling. Water was azeotroped off until (about 45 minutes) no more came over. The dry solution was filtered through Celite (to remove precipitated salt and any other solids present) and steam stripped. The product resin was drained from the reactor as a melt, in quantitative yield—based on the trisphenol charged. It had an ionic chloride content below 10 ppm, a hydrolyzable chloride content of about 200 ppm and a melt viscosity of about 300 centipoises.

The process of both Examples 1 and 2 are considered generally suitable for the preparation of low halide content epoxy resins from either preformed or nascent "epoxidation" products of polyfunctional aromatic phenols or amines, or of heterocyclic compounds having two or more >N-H groups in the ring, with epihalohydrins. A wide variety of such epoxidation products (polyfunctional glycidyloxy and/or glycidylamino—including diglycidylamino-derivatives) are known and no useful purpose would be served by comprehensively listing them here. However, the types of epihalohydrin-reactive compounds listed below are both preferred and representative of the broad class of such compounds from which suitable epoxidation products may be prepared.

Polyhydroxy benzenes, such as 1,2,- 1,3- and 1,4-dihydroxy or 1,3,5-trihydroxybenzene, for example.

1,6-Diglycidylphenol.

Di-nuclear phenols and phenolic hydroxy-terminated polymeric adducts thereof with their diglycidyl ethers; the two phenyl rings being linked by a valence bond, an alkylene, alkenylene, cycloalkylene, cycloalkenylene, phenylene or an —O—, —S—, —$SO_2$—, —SO—, —CO— or

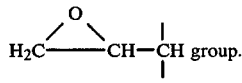

group.

$C_1$–$C_6$ alkanes substituted with 3 or 4 hydroxyphenyl groups (optionally substituted with non-interfering groups, such as—for example—alkyl, alkoxy or chloro groups).

Trialkyl benzenes in which each alkyl group is substituted by a hydroxyphenyl group.

Phenol/formaldehyde and cresol/formaldehyde novolacs comprising from 3 to 7 and preferably from 3 to 5 hydroxyphenylene groups, bisphenol A/formaldehyde novolacs containing up to eight phenolic hydroxyls.

Para-aminophenol, methylene dianiline and 4,4′-diaminophenyl sulfone.

5,5-Dialkylhydantoins and 3-(2-hydroxypropyl)hydantoin.

Isocyanuric acid.

What is claimed is:

1. The method of reducing the hydrolyzable chloride content of an epoxidation product, without substantially altering it otherwise, which comprises
    (1) providing a two-phase mixture of
        (a) an organic phase which is a solution of said product in a solvent having the characteristics of a blend of from about 40 to about 55 weight % methylethylketone and from about 60 to about 45 weight % toluene, and
        (b) an aqueous solution of from about 1 to about 3 equivalents of base per equivalent of hydrolyzable chloride in said product, the amount of water in said solution being such that the base concentration therein will not be less than equivalent to 4 weight % aqueous NaOH after completion of the following step and
    (2) intimately intercontacting said phases, at an elevated temperature, until the hydrolyzable chloride content of said product has decreased to a satisfactory extent.

2. The process of claim 1 in which said product has been prepared by the reaction of a base with an adduct of an epihalohydrin and a polyfunctional phenol, aromatic amine or an N-heterocycle comprising two or more ring nitrogens to which active hydrogens are attached.

3. The process of claim 2 in which said product initially contains in excess of 200 ppm of hydrolyzable chloride.

4. The process of claim 3 in which said product comprises a substantial proportion of oligomeric species of epoxides formed from several molecules of said polyfunctional compound during said reaction.

5. The process of claim 4 in which said polyfunctional phenol is a di- or tri-hydroxy benzene, bisphenol F or A, a phenol/ or cresol/formaldehyde novolac containing from 3 to 5 hydroxyphenylene groups, a $C_1$–$C_3$ alkane substituted with 3 or 4 hydroxyphenyl groups, 1,6-diglycidyl phenol, a bisphenol A/formaldehyde novolac containing up to eight phenolic hydroxyls or p-aminophenol.

6. The process of claim 4 in which said aromatic amine is methylene dianiline.

7. The process of claim 4 in which said N-heterocycle is a 5,5-dialkylhydantoin, 3-(2-hydroxypropyl)hydantoin or isocyanuric acid.

8. The process of claim 5 in which said polyphenol is a tri(hydroxyphenyl)methane or a phenol/or cresol/formaldehyde novolac containing from 3 to 5 hydroxyphenylene groups and said epihalohydrin is epichlorohydrin.

9. The process of claim 8 in which said polyphenol is 2,4′,4″-tri(hydroxyphenyl)methane, said base is NaOH and said solvent is a 1:1 by weight blend of MEK and toluene.

10. The process of claim 9 in which the organic phase of the final dehydrochlorination mixture is separated, diluted with more 1:1 MEK/toluene, neutralized with carbon dioxide, dried by azeotropic distillation, filtered and the resulting filtrate steam-stripped.

11. The process of claim 10 in which said epoxidation product is prepared in-situ by reacting said polyphenol in 1:1 MEK/toluene with from about 1.45 to about 1.55 equivalents of epichlorohydrin and from about 1.60 to about 1.70 equivalents of NaOH per phenolic hydroxyl, adding more 1:1 MEK/toluene and water, separating the organic phase, azeotroping to remove essentially all of the unreacted epichlorohydrin and some of the water, to provide said epoxidation product as the resulting solution.

* * * * *